US009060972B2

(12) United States Patent
Liu

(10) Patent No.: US 9,060,972 B2
(45) Date of Patent: *Jun. 23, 2015

(54) RECOMBINANT HEMAGGLUTININ PROTEIN OF INFLUENZA VIRUS AND VACCINE CONTAINING THE SAME

(76) Inventor: George Dacai Liu, Collegeville, PA (US)

(*) Notice: Subject to any disclaimer, the term of this patent is extended or adjusted under 35 U.S.C. 154(b) by 458 days.

This patent is subject to a terminal disclaimer.

(21) Appl. No.: 13/279,253

(22) Filed: Oct. 22, 2011

(65) Prior Publication Data

US 2012/0107911 A1    May 3, 2012

Related U.S. Application Data

(60) Provisional application No. 61/408,576, filed on Oct. 30, 2010.

(51) Int. Cl.
| | | |
|---|---|---|
| *C07K 14/11* | (2006.01) | |
| *A61K 39/145* | (2006.01) | |
| *A61K 38/02* | (2006.01) | |
| *C07K 19/00* | (2006.01) | |
| *A61K 35/76* | (2015.01) | |
| *C07K 2/00* | (2006.01) | |
| *A61K 39/00* | (2006.01) | |

(52) U.S. Cl.
CPC .............. *A61K 39/145* (2013.01); *A61K 38/02* (2013.01); *C07K 19/00* (2013.01); *A61K 35/76* (2013.01); *C07K 2/00* (2013.01); *A61K 2039/5252* (2013.01); *A61K 2039/55566* (2013.01); *C07K 2319/00* (2013.01); *C07K 2319/03* (2013.01); *C07K 2319/72* (2013.01); *C12N 2760/16134* (2013.01)

(58) Field of Classification Search
None
See application file for complete search history.

(56) References Cited

U.S. PATENT DOCUMENTS

| | | | |
|---|---|---|---|
| 6,716,429 B1 * | 4/2004 | Sodroski et al. | 424/188.1 |
| 7,105,655 B2 * | 9/2006 | Sodroski et al. | 536/23.72 |
| 2002/0168392 A1 * | 11/2002 | Manners et al. | 424/405 |
| 2005/0106177 A1 * | 5/2005 | Sodroski et al. | 424/208.1 |

OTHER PUBLICATIONS

Nilsson et al., J. Mol. Biol., 1998, 284:1165-1175.*
Iqbalsyah et al., Protein Science, 2006, 15:1945-1950.*

* cited by examiner

*Primary Examiner* — Nicole Kinsey White
(74) *Attorney, Agent, or Firm* — George Dacai Liu

(57) ABSTRACT

The present invention provides a recombinant hemagglutinin antigenic protein, a virus-like particle and a recombinant influenza virus. The present invention further provides a vaccine comprising the recombinant hemagglutinin antigenic protein, the virus-like particle or recombinant influenza virus.

12 Claims, 1 Drawing Sheet

| HA1 | | LH | | MPH | TMD | CPD |

328

SEQUENCE LISTING

<160> NUMBER OF SEQ ID NOS: 23

<210> SEQ ID NO 1
<211> LENGTH: 1717
<212> TYPE: DNA
<213> ORGANISM: Influenza A virus

<400> SEQUENCE: 1

```
atcatgaaga ccatcattgc tttgagctac attttctgtc tggctctcgg ccaagacctt      60
ccaggaaatg acaacagcac agcaacgctg tgcctgggac atcatgcggt gccaaacgga     120
acactagtga aaacaatcac agatgatcag attgaagtga ctaatgctac tgagctagtt     180
cagagctcct caacggggaa aatatgcaac aatcctcatc gaatccttga tggaatagac     240
tgcacactga tagatgctct attggggac cctcattgtg atgttttca aaatgagaca      300 tgggacctt tcgttgaacg cagcaaagct ttcagcaact gttaccctta tgatgtgcca     360
gattatgcct cccttaggtc actagttgcc tcgtcaggca ctctggagtt tatcactgag     420
ggtttcactt ggactgggt cactcagaat gggggaagca atgcttgcaa aaggggacct     480
ggtagcggtt ttttcagtag actgaactgg ttgaccaaat caggaagcac atatccagtg     540
ctgaacgtga ctatgccaaa caatgacaat tttgacaaac tatacatttg gggggttcac     600 caccccgagca cgaaccaaga acaaaccagc ctgtatgttc aagcatcagg gagagtcaca     660
gtctctacca gaagaagcca gcaaactata atcccgaata tcgggtccag accctgggta     720
aggggtctgt ctagtagaat aagcatctat tggacaatag ttaagccggg agacgtactg     780
```

-continued

```
gtaattaata gtaatgggaa cctaatcgct cctcggggtt atttcaaaat gcgcactggg    840
aaaagctcaa taatgaggtc agatgcacct attgatacct gtatttctga atgcatcact    900
ccaaatggaa gcattcccaa tgacaagccc tttcaaaacg taaacaagat cacatatgga    960
gcatgcccca gtatgttaa gcaaaacacc ctgaagttgg caacagggat gcggaatgta    1020
ccagagaaac aaactagagg cctattcggc gcaatagcag gtttcataga aatggttgg    1080 gagggaatga tagacggttg gtacggtttc aggcatcaaa attctgaggg cacaggacaa    1140
gcagcagatc ttaaaagcac tcaagcagcc atcgaccaaa tcaatgggaa attgaacagg    1200
gtaatcgaga agacgaacga gaaattccat caaatcgaaa aggaattctc agaagtagaa    1260
gggagaattc aggacctcga gaaatacgtt gaagacacta aaatagatct ctggtcttac    1320
aatgcggagc ttcttgtcgc tctggagaat caacatacaa ttgacctgac tgactcggaa    1380
atgaacaagc tgtttgaaaa acaaggagg caactgaggg aaaatgctga agacatgggc    1440
aatggttgct tcaaaatata ccacaaatgt gacaacgctt gcatagagtc aatcagaaat    1500
gggacttatg accatgatgt atacagagac gaagcattaa caaccggtt tcagatcaaa    1560 ggtgttgaac tgaagtctgg atacaaagac tggatcctgt ggatttcctt tgccatatca    1620 tgcttttgc tttgtgttgt tttgctgggg ttcatcatgt gggcctgcca gagaggcaac    1680
attaggtgca catttgcat ttgagtgtat tagtaat                              1717
```

<210> SEQ ID NO 2
<211> LENGTH: 566
<212> TYPE: PRT
<213> ORGANISM: Influenza A virus

<400> SEQUENCE: 2

```
Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asp Asp
        35                  40                  45

Gln Ile Glu Val Thr Asn Ala Thr Glu Leu Val Gln Ser Ser Ser Thr
    50                  55                  60

Gly Lys Ile Cys Asn Asn Pro His Arg Ile Leu Asp Gly Ile Asp Cys
65                  70                  75                  80

Thr Leu Ile Asp Ala Leu Leu Gly Asp Pro His Cys Asp Val Phe Gln
                85                  90                  95

Asn Glu Thr Trp Asp Leu Phe Val Glu Arg Ser Lys Ala Phe Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Ile Thr Glu Gly Phe Thr Trp Thr
    130                 135                 140

Gly Val Thr Gln Asn Gly Gly Ser Asn Ala Cys Lys Arg Gly Pro Gly
145                 150                 155                 160

Ser Gly Phe Phe Ser Arg Leu Asn Trp Leu Thr Lys Ser Gly Ser Thr
                165                 170                 175

Tyr Pro Val Leu Asn Val Thr Met Pro Asn Asn Asp Asn Phe Asp Lys
            180                 185                 190

Leu Tyr Ile Trp Gly Val His His Pro Ser Thr Asn Gln Glu Gln Thr
        195                 200                 205
```

```
Ser Leu Tyr Val Gln Ala Ser Gly Arg Val Thr Val Ser Thr Arg Arg
    210                 215                 220

Ser Gln Gln Thr Ile Ile Pro Asn Ile Gly Ser Arg Pro Trp Val Arg
225                 230                 235                 240

Gly Leu Ser Ser Arg Ile Ser Ile Tyr Trp Thr Ile Val Lys Pro Gly
                245                 250                 255

Asp Val Leu Val Ile Asn Ser Asn Gly Asn Leu Ile Ala Pro Arg Gly
                260                 265                 270

Tyr Phe Lys Met Arg Thr Gly Lys Ser Ser Ile Met Arg Ser Asp Ala
            275                 280                 285

Pro Ile Asp Thr Cys Ile Ser Glu Cys Ile Thr Pro Asn Gly Ser Ile
290                 295                 300

Pro Asn Asp Lys Pro Phe Gln Asn Val Asn Lys Ile Thr Tyr Gly Ala
305                 310                 315                 320

Cys Pro Lys Tyr Val Lys Gln Asn Thr Leu Lys Leu Ala Thr Gly Met
                325                 330                 335

Arg Asn Val Pro Glu Lys Gln Thr Arg Gly Leu Phe Gly Ala Ile Ala
            340                 345                 350

Gly Phe Ile Glu Asn Gly Trp Glu Gly Met Ile Asp Gly Trp Tyr Gly
        355                 360                 365

Phe Arg His Gln Asn Ser Glu Gly Thr Gly Gln Ala Ala Asp Leu Lys
370                 375                 380

Ser Thr Gln Ala Ala Ile Asp Gln Ile Asn Gly Lys Leu Asn Arg Val
385                 390                 395                 400

Ile Glu Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
    450                 455                 460

Glu Lys Thr Arg Arg Gln Leu Arg Glu Asn Ala Glu Asp Met Gly Asn
465                 470                 475                 480

Gly Cys Phe Lys Ile Tyr His Lys Cys Asp Asn Ala Cys Ile Glu Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
530                 535                 540

Val Val Leu Leu Gly Phe Ile Met Trp Ala Cys Gln Arg Gly Asn Ile
545                 550                 555                 560

Arg Cys Asn Ile Cys Ile
                565

<210> SEQ ID NO 3
<211> LENGTH: 4
<212> TYPE: PRT
<213> ORGANISM: Artificial
<220> FEATURE:
<223> OTHER INFORMATION: two-cysteine mini-domain 1
<220> FEATURE:
<221> NAME/KEY: misc_feature
<222> LOCATION: (2)..(3)
```

-continued

```
<223> OTHER INFORMATION: Xaa can be any naturally occurring amino acid

<400> SEQUENCE: 3

Cys Xaa Xaa Cys
1

<210> SEQ ID NO 4
<211> LENGTH: 5
<212> TYPE: PRT
<213> ORGANISM: Artificial
<220> FEATURE:
<223> OTHER INFORMATION: two-cysteine mini-domain 2
<220> FEATURE:
<221> NAME/KEY: misc_feature
<222> LOCATION: (2)..(4)
<223> OTHER INFORMATION: Xaa can be any naturally occurring amino acid

<400> SEQUENCE: 4

Cys Xaa Xaa Xaa Cys
1               5

<210> SEQ ID NO 5
<211> LENGTH: 6
<212> TYPE: PRT
<213> ORGANISM: Artificial
<220> FEATURE:
<223> OTHER INFORMATION: two-cysteine mini-domain 3
<220> FEATURE:
<221> NAME/KEY: misc_feature
<222> LOCATION: (2)..(5)
<223> OTHER INFORMATION: Xaa can be any naturally occurring amino acid

<400> SEQUENCE: 5

Cys Xaa Xaa Xaa Xaa Cys
1               5

<210> SEQ ID NO 6
<211> LENGTH: 27
<212> TYPE: PRT
<213> ORGANISM: Artificial
<220> FEATURE:
<223> OTHER INFORMATION: Influenza A virus HA transmembrane domain of H1

<400> SEQUENCE: 6

Gln Ile Leu Ala Ile Tyr Ser Thr Val Ala Ser Ser Leu Val Leu Leu
1               5                   10                  15

Val Ser Leu Gly Ala Ile Ser Phe Trp Met Cys
            20                  25

<210> SEQ ID NO 7
<211> LENGTH: 27
<212> TYPE: PRT
<213> ORGANISM: Artificial
<220> FEATURE:
<223> OTHER INFORMATION: Influenza A virus HA transmembrane domain of H2

<400> SEQUENCE: 7

Gln Ile Leu Ala Ile Tyr Ala Thr Val Ala Gly Ser Leu Ser Leu Ala
1               5                   10                  15

Ile Met Ile Ala Gly Ile Ser Phe Trp Met Cys
            20                  25

<210> SEQ ID NO 8
<211> LENGTH: 27
<212> TYPE: PRT
<213> ORGANISM: Artificial
<220> FEATURE:
```

-continued

<223> OTHER INFORMATION: Influenza A virus HA transmembrane domain of H3

<400> SEQUENCE: 8

Asp Trp Ile Leu Trp Ile Ser Phe Ala Ile Ser Cys Phe Leu Leu Cys
1               5                   10                  15

Val Val Leu Leu Gly Phe Ile Met Trp Ala Cys
            20                  25

<210> SEQ ID NO 9
<211> LENGTH: 27
<212> TYPE: PRT
<213> ORGANISM: Artificial
<220> FEATURE:
<223> OTHER INFORMATION: Influenza A virus HA transmembrane domain of H4

<400> SEQUENCE: 9

Asp Ile Ile Leu Trp Ile Ser Phe Ser Ile Ser Cys Phe Leu Leu Val
1               5                   10                  15

Ala Leu Leu Leu Ala Phe Ile Leu Trp Ala Cys
            20                  25

<210> SEQ ID NO 10
<211> LENGTH: 27
<212> TYPE: PRT
<213> ORGANISM: Artificial
<220> FEATURE:
<223> OTHER INFORMATION: Influenza A virus HA transmembrane domain of H5

<400> SEQUENCE: 10

Gln Ile Leu Ser Ile Tyr Ser Thr Val Ala Ser Ser Leu Ala Leu Ala
1               5                   10                  15

Ile Met Val Ala Gly Leu Ser Leu Trp Met Cys
            20                  25

<210> SEQ ID NO 11
<211> LENGTH: 27
<212> TYPE: PRT
<213> ORGANISM: Artificial
<220> FEATURE:
<223> OTHER INFORMATION: Influenza A virus HA transmembrane domain of H6

<400> SEQUENCE: 11

Gln Ile Leu Ala Ile Tyr Ser Thr Val Ser Ser Ser Leu Val Leu Val
1               5                   10                  15

Gly Leu Ile Ile Ala Met Gly Leu Trp Met Cys
            20                  25

<210> SEQ ID NO 12
<211> LENGTH: 27
<212> TYPE: PRT
<213> ORGANISM: Artificial
<220> FEATURE:
<223> OTHER INFORMATION: Influenza A virus HA transmembrane domain of H7

<400> SEQUENCE: 12

Asp Val Ile Leu Trp Phe Ser Phe Gly Ala Ser Cys Phe Ile Leu Leu
1               5                   10                  15

Ala Ile Ala Met Gly Leu Val Phe Ile Cys Val
            20                  25

<210> SEQ ID NO 13
<211> LENGTH: 27
<212> TYPE: PRT
<213> ORGANISM: Artificial

```
<220> FEATURE:
<223> OTHER INFORMATION: Influenza A virus HA transmembrane domain of H8

<400> SEQUENCE: 13

Lys Ile Leu Ser Ile Tyr Ser Thr Val Ala Ala Ser Leu Cys Leu Ala
1               5                   10                  15

Ile Leu Ile Ala Gly Gly Leu Ile Leu Gly Met
            20                  25

<210> SEQ ID NO 14
<211> LENGTH: 27
<212> TYPE: PRT
<213> ORGANISM: Artificial
<220> FEATURE:
<223> OTHER INFORMATION: Influenza A virus HA transmembrane domain of H9

<400> SEQUENCE: 14

Lys Ile Leu Ser Ile Tyr Ser Thr Val Ala Ala Ser Leu Cys Leu Ala
1               5                   10                  15

Ile Leu Ile Ala Gly Gly Leu Ile Leu Gly Met
            20                  25

<210> SEQ ID NO 15
<211> LENGTH: 27
<212> TYPE: PRT
<213> ORGANISM: Artificial
<220> FEATURE:
<223> OTHER INFORMATION: Influenza A virus HA transmembrane domain of
      H10

<400> SEQUENCE: 15

Asp Ile Ile Leu Trp Phe Ser Phe Gly Ala Ser Cys Phe Ile Leu Leu
1               5                   10                  15

Ala Val Val Met Gly Leu Val Phe Phe Cys Leu
            20                  25

<210> SEQ ID NO 16
<211> LENGTH: 27
<212> TYPE: PRT
<213> ORGANISM: Artificial
<220> FEATURE:
<223> OTHER INFORMATION: Influenza A virus HA transmembrane domain of
      H11

<400> SEQUENCE: 16

Lys Ile Leu Ser Ile Tyr Ser Cys Ile Ala Ser Ser Leu Val Leu Ala
1               5                   10                  15

Ala Ile Ile Met Gly Phe Ile Phe Trp Ala Cys
            20                  25

<210> SEQ ID NO 17
<211> LENGTH: 27
<212> TYPE: PRT
<213> ORGANISM: Artificial
<220> FEATURE:
<223> OTHER INFORMATION: Influenza A virus HA transmembrane domain of
      H12

<400> SEQUENCE: 17

Lys Ile Leu Ser Ile Tyr Ser Ser Val Ala Ser Ser Leu Val Leu Leu
1               5                   10                  15

Leu Met Ile Ile Gly Gly Phe Ile Phe Gly Cys
            20                  25
```

```
<210> SEQ ID NO 18
<211> LENGTH: 27
<212> TYPE: PRT
<213> ORGANISM: Artificial
<220> FEATURE:
<223> OTHER INFORMATION: Influenza A virus HA transmembrane domain of
      H13

<400> SEQUENCE: 18

Lys Ala Leu Ser Ile Tyr Ser Cys Ile Ala Ser Ser Val Val Leu Val
1               5                   10                  15

Gly Leu Ile Leu Ser Phe Ile Met Trp Ala Cys
            20                  25

<210> SEQ ID NO 19
<211> LENGTH: 27
<212> TYPE: PRT
<213> ORGANISM: Artificial
<220> FEATURE:
<223> OTHER INFORMATION: Influenza A virus HA transmembrane domain of
      H14

<400> SEQUENCE: 19

Asp Ile Ile Leu Trp Ile Ser Phe Ser Met Ser Cys Phe Val Phe Val
1               5                   10                  15

Ala Leu Ile Leu Gly Phe Val Leu Trp Ala Cys
            20                  25

<210> SEQ ID NO 20
<211> LENGTH: 27
<212> TYPE: PRT
<213> ORGANISM: Artificial
<220> FEATURE:
<223> OTHER INFORMATION: Influenza A virus HA transmembrane domain of
      H15

<400> SEQUENCE: 20

Asp Val Ile Leu Trp Phe Ser Phe Gly Ala Ser Cys Val Met Leu Leu
1               5                   10                  15

Ala Ile Ala Met Gly Leu Ile Phe Met Cys Val
            20                  25

<210> SEQ ID NO 21
<211> LENGTH: 27
<212> TYPE: PRT
<213> ORGANISM: Artificial
<220> FEATURE:
<223> OTHER INFORMATION: Influenza A virus HA transmembrane domain of
      H16

<400> SEQUENCE: 21

Lys Val Leu Ser Ile Tyr Ser Cys Ile Ala Ser Ser Ile Val Leu Val
1               5                   10                  15

Gly Leu Ile Leu Ala Phe Ile Met Trp Ala Cys
            20                  25

<210> SEQ ID NO 22
<211> LENGTH: 565
<212> TYPE: PRT
<213> ORGANISM: Influenza A virus

<400> SEQUENCE: 22

Met Lys Ala Asn Leu Leu Val Leu Leu Cys Ala Leu Ala Ala Ala Asp
1               5                   10                  15

Ala Asp Thr Ile Cys Ile Gly Tyr His Ala Asn Asn Ser Thr Asp Thr
```

```
              20                  25                  30
Val Asp Thr Val Leu Glu Lys Asn Val Thr Val Thr His Ser Val Asn
            35                  40                  45
Leu Leu Glu Asp Ser His Asn Gly Lys Leu Cys Arg Leu Lys Gly Ile
        50                  55                  60
Ala Pro Leu Gln Leu Lys Cys Asn Ile Ala Gly Trp Leu Leu Gly
65                  70                  75                  80
Asn Pro Glu Cys Asp Pro Leu Leu Pro Val Arg Ser Trp Ser Tyr Ile
                85                  90                  95
Val Glu Thr Pro Asn Ser Glu Asn Gly Ile Cys Tyr Pro Gly Asp Phe
            100                 105                 110
Ile Asp Tyr Glu Glu Leu Arg Glu Gln Leu Ser Ser Val Ser Ser Phe
        115                 120                 125
Glu Arg Phe Glu Ile Phe Pro Lys Glu Ser Ser Trp Pro Asn His Asn
    130                 135                 140
Thr Asn Gly Val Thr Ala Ala Cys Ser His Glu Gly Lys Ser Ser Phe
145                 150                 155                 160
Tyr Arg Asn Leu Leu Trp Leu Thr Glu Lys Glu Gly Ser Tyr Pro Lys
                165                 170                 175
Leu Lys Asn Ser Tyr Val Asn Lys Lys Gly Lys Glu Val Leu Val Leu
            180                 185                 190
Trp Gly Ile His His Pro Pro Asn Ser Lys Glu Gln Gln Asn Leu Tyr
        195                 200                 205
Gln Asn Glu Asn Ala Tyr Val Ser Val Val Thr Ser Asn Tyr Asn Arg
    210                 215                 220
Arg Phe Thr Pro Glu Ile Ala Glu Arg Pro Lys Val Arg Asp Gln Ala
225                 230                 235                 240
Gly Arg Met Asn Tyr Tyr Trp Thr Leu Leu Lys Pro Gly Asp Thr Ile
                245                 250                 255
Ile Phe Glu Ala Asn Gly Asn Leu Ile Ala Pro Met Tyr Ala Phe Ala
            260                 265                 270
Leu Ser Arg Gly Phe Gly Ser Gly Ile Ile Thr Ser Asn Ala Ser Met
        275                 280                 285
His Glu Cys Asn Thr Lys Cys Gln Thr Pro Leu Gly Ala Ile Asn Ser
    290                 295                 300
Ser Leu Pro Tyr Gln Asn Ile His Pro Val Thr Ile Gly Glu Cys Pro
305                 310                 315                 320
Lys Tyr Val Arg Ser Ala Lys Leu Arg Met Val Thr Gly Leu Arg Asn
                325                 330                 335
Ile Pro Ser Ile Gln Ser Arg Gly Leu Phe Gly Ala Ile Ala Gly Phe
            340                 345                 350
Ile Glu Gly Gly Trp Thr Gly Met Ile Asp Gly Trp Tyr Gly Tyr His
        355                 360                 365
His Gln Asn Glu Gln Gly Ser Gly Tyr Ala Ala Asp Gln Lys Ser Thr
    370                 375                 380
Gln Asn Ala Ile Asn Gly Ile Thr Asn Lys Val Asn Thr Val Ile Glu
385                 390                 395                 400
Lys Met Asn Ile Gln Phe Thr Ala Val Gly Lys Glu Phe Asn Lys Leu
                405                 410                 415
Glu Lys Arg Met Glu Asn Leu Asn Lys Lys Val Asp Asp Gly Phe Leu
            420                 425                 430
Asp Ile Trp Thr Tyr Asn Ala Glu Leu Leu Val Leu Leu Glu Asn Glu
        435                 440                 445
```

```
Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asp Asn Glu Cys Met Glu Ser Val Arg
                485                 490                 495

Asn Gly Thr Tyr Asp Tyr Pro Lys Tyr Ser Glu Glu Ser Lys Leu Asn
                500                 505                 510

Arg Glu Lys Val Asp Gly Val Lys Leu Glu Ser Met Gly Ile Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
                565

<210> SEQ ID NO 23
<211> LENGTH: 565
<212> TYPE: PRT
<213> ORGANISM: Artificial
<220> FEATURE:
<223> OTHER INFORMATION: Influenza A virus (A/Puerto Rico/8-
      V24/1934(H1N1), two cysteine substitution in the transmembrane
      domain (H12C)

<400> SEQUENCE: 23

Met Lys Ala Asn Leu Leu Val Leu Leu Cys Ala Leu Ala Ala Ala Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Ile
    50                  55                  60

Ala Pro Leu Gln Leu Gly Lys Cys Asn Ile Ala Gly Trp Leu Leu Gly
65                  70                  75                  80

Asn Pro Glu Cys Asp Pro Leu Leu Pro Val Arg Ser Trp Ser Tyr Ile
                85                  90                  95

Val Glu Thr Pro Asn Ser Glu Asn Gly Ile Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Asn
    130                 135                 140

Thr Asn Gly Val Thr Ala Ala Cys Ser His Glu Gly Lys Ser Ser Phe
145                 150                 155                 160

Tyr Arg Asn Leu Leu Trp Leu Thr Glu Lys Glu Gly Ser Tyr Pro Lys
                165                 170                 175

Leu Lys Asn Ser Tyr Val Asn Lys Lys Gly Lys Glu Val Leu Val Leu
            180                 185                 190

Trp Gly Ile His His Pro Pro Asn Ser Lys Glu Gln Gln Asn Leu Tyr
        195                 200                 205

Gln Asn Glu Asn Ala Tyr Val Ser Val Val Thr Ser Asn Tyr Asn Arg
    210                 215                 220
```

-continued

```
Arg Phe Thr Pro Glu Ile Ala Glu Arg Pro Lys Val Arg Asp Gln Ala
225                 230                 235                 240

Gly Arg Met Asn Tyr Tyr Trp Thr Leu Leu Lys Pro Gly Asp Thr Ile
            245                 250                 255

Ile Phe Glu Ala Asn Gly Asn Leu Ile Ala Pro Met Tyr Ala Phe Ala
            260                 265                 270

Leu Ser Arg Gly Phe Gly Ser Gly Ile Ile Thr Ser Asn Ala Ser Met
        275                 280                 285

His Glu Cys Asn Thr Lys Cys Gln Thr Pro Leu Gly Ala Ile Asn Ser
    290                 295                 300

Ser Leu Pro Tyr Gln Asn Ile His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Ser Ile Gln Ser Arg Gly Leu Phe Gly Ala Ile Ala Gly Phe
                340                 345                 350

Ile Glu Gly Gly Trp Thr Gly Met Ile Asp Gly Trp Tyr Gly Tyr His
            355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Thr Val Ile Glu
385                 390                 395                 400

Lys Met Asn Ile Gln Phe Thr Ala Val Gly Lys Glu Phe Asn Lys Leu
                405                 410                 415

Glu Lys Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
            435                 440                 445

Arg Thr Leu Asp Phe His Asp Ser Asn Val Lys Asn Leu Tyr Glu Lys
        450                 455                 460

Val Lys Ser Gln Leu Lys Asn Asn Ala Lys Glu Ile Gly Asn Gly Cys
465                 470                 475                 480

Phe Glu Phe Tyr His Lys Cys Asp Asn Glu Cys Met Glu Ser Val Arg
                485                 490                 495

Asn Gly Thr Tyr Asp Tyr Pro Lys Tyr Ser Glu Glu Ser Lys Leu Asn
            500                 505                 510

Arg Glu Lys Val Asp Gly Val Lys Leu Glu Ser Met Gly Ile Tyr Gln
        515                 520                 525

Ile Leu Ala Ile Tyr Ser Thr Val Ala Cys Ser Leu Val Cys Leu Val
530                 535                 540

Ser Leu Gly Ala Ile Ser Phe Trp Met Cys Ser Asn Gly Ser Leu Gln
545                 550                 555                 560

Cys Arg Ile Cys Ile
                565
```

RECOMBINANT HEMAGGLUTININ PROTEIN OF INFLUENZA VIRUS AND VACCINE CONTAINING THE SAME

CROSS REFERENCE TO RELATED APPLICATIONS

The present application claims the priority of U.S. provisional application No. 61/408,576 filed on Oct. 30, 2010, entitled of "Recombinant hemagglutinin protein of influenza virus and vaccine containing the same", the disclosure of which is herein incorporated in its entirety.

FIELD OF THE INVENTION

The present invention relates to recombinant hemagglutinin proteins of influenza virus and vaccines comprising the recombinant hemagglutinin proteins.

BACKGROUND OF THE INVENTION

Influenza A viruses are responsible for the major pandemics of influenza in the last century and also the causative agents for most of the annual outbreaks of epidemic influenza. The WHO estimates that epidemic influenza affects approximately 5-15% of the global population annually, and is responsible for up to 3-5 million cases of severe disease and 500,000 deaths per year. WHO Influenza Fact sheet 211. World Health Organisation, Geneva, Switzerland (2003).

Influenza A virus is a member of the Orthomyxovirus family, and has a wide host range, including humans, horses, dogs, birds, and pigs. It is an enveloped, negative-sense RNA virus composed of a set of 8 RNA segments (abbreviated as PB2, PB1, PA, HA, NP, NA, M and NS) encoding at least 10 viral proteins. The HA segment encodes the hemagglutinin (HA) protein. The NA segment encodes the neuraminidase (NA). Based on serological classification, 16 HA subtypes (designated as H1 through H16) and 9 NA subtypes (designated as N1 through N9) have been thus far identified. Subtypes of influenza A that are currently circulating among people worldwide include H1N1, H1N2, and H3N2 viruses; H5N1 and H9N2 are circulating in birds such chickens; and H1N1 and H3N2 are circulating in pigs.

Current inactivated influenza vaccines are trivalent, containing 15±g HA of two influenza A (H1N1 and H3N2) subtypes and one influenza B strain. The basic technology and principles of vaccine production have remained much the same since their first introduction into clinical uses in the 1940s. The conventional wisdoms have focused on the optimization of production procedures to produce a conventional virus preparation with the maximum amount of HA proteins. In addition, influenza vaccines are standardized solely on the basis of HA content.

Vaccine efficacy declines as the antigenic relatedness between the circulating viruses and the viruses selected for the vaccine becomes more distant within the same subtype. Influenza virus undergoes two types of antigenic variation, "antigenic drift" and "antigenic shift". Antigenic drift is part of the continuing occurrence of new influenza strains that differ from their ancestors by mutations in the HA and NA genes. The amount of change can be subtle or dramatic. The second type of antigenic variation is "antigenic shift". A genetic shift can occur when two different influenza viruses, co-infecting the same host, exchange a whole genomic segment. This could result in a "reassortant" virus with a novel gene constellation and consequently with new properties. A genetic shift can also occur when a virus subtype crosses the species barrier directly without reassortment in an intermediate host. The antigenic variation of influenza viruses forms the primary basis for the occurrence of annual influenza epidemics and occasional pandemics and necessitates constant evolution of vaccine composition. For influenza vaccines, strain selection of the three viruses to be included in the annual seasonal vaccine now occurs twice a year at the WHO. While the selected strains are usually antigenically close to circulating strains, in some years they are not. Furthermore, avian H5N1 and swine H1N1 in recent years caused pandemic fears. Therefore, there is a need to have vaccines that will produce broadened protective immunity.

SUMMARY OF THE INVENTION

One aspect of the present invention provides a recombinant HA antigenic protein. In one embodiment, the recombinant HA antigenic protein comprises an extracellular domain with major antigenic epitopes; and a long helix (LH); wherein at least one two-cysteine mini-domain selected from CxxC (SEQ ID NO 3), CxxxC (SEQ ID NO 4) or CxxxxC (SEQ ID NO 5) is present in the LH, where x represents any amino acids; whereby when the recombinant HA antigenic protein forms a trimer, the two cysteines in the LH form a tandem disulfide bond belt, covalently tighting the trimer.

In another embodiment of the recombinant HA antigenic protein, it further comprises a membrane-proximity helix (MPH); a transmembrane domain (TMD); and a cytoplasmic domain (CPD); wherein the at least one two-cysteine mini-domain selected from CxxC (SEQ ID NO 3), CxxxC (SEQ ID NO 4) or CxxxxC (SEQ ID NO 5) is present in the LH, MPH or TMD, and wherein CFLLC is excluded if the CxxxC (SEQ ID NO 4) is to be present in the TMD; whereby when the recombinant HA antigenic protein forms a trimer, the two cysteines in the LH, MPH or TMD form a tandem disulfide bond belt, covalently tightening the trimer.

In another embodiment of the recombinant HA antigenic protein, the TMD or CPD are derived from a HA protein that is not the same HA protein providing the extracellular domain and LH.

In another embodiment of the recombinant HA antigenic protein, the TMD or CPD are artificially synthetic peptides or derived from a non-HA protein forming trimers in its native configuration.

In another embodiment of the recombinant HA antigenic protein, the recombinant HA antigenic protein is encoded by a DNA sequence, and the DNA sequence is cloned into an in vivo expression vector; so that the recombinant HA expression vector is used as a DNA vaccine against influenza virus infection.

In another embodiment of the recombinant HA antigenic protein, it is used in a vaccine against influenza virus infection.

Another aspect of the present invention provides a virus-like particle. In one embodiment, the virus-like particle comprises a recombinant HA antigenic protein, wherein the recombinant HA antigenic protein comprises an extracellular domain with major antigenic epitopes; a long helix (LH); a membrane-proximity helix (MPH); a transmembrane domain (TMD); and a cytoplasmic domain(CPD); wherein at least one two-cysteine mini-domain selected from CxxC (SEQ ID NO 3), CxxxC (SEQ ID NO 4) or CxxxxC (SEQ ID NO 5) is present in the LH, MPH or TMD where x represents any amino acids; and wherein CFLLC is excluded if the CxxxC (SEQ ID NO 4) is to be present in the TMD; whereby when the recombinant HA antigenic protein forms a trimer, the two cysteines in the LH, MPH or TMD form a tandem disulfide bond belt, covalently tightening the trimer.

In another embodiment of the virus-like particle, the TMD or CPD are derived from a HA protein that is not the same HA protein providing the extracellular domain and LH.

In another embodiment of the virus-like particle, the TMD or CPD are artificially synthetic peptides or derived from a non-HA protein forming trimers in its native configuration.

In another embodiment of the virus-like particle, the virus-like particle is used in a vaccine against influenza virus infection.

Another aspect of the present invention provides a recombinant influenza virus. In one embodiment, the recombinant influenza virus comprises a recombinant HA antigenic protein, wherein the recombinant HA antigenic protein comprises an extracellular domain with major antigenic epitopes; a long helix (LH); a membrane-proximity helix (MPH); a transmembrane domain (TMD); and a cytoplasmic domain (CPD); wherein at least one two-cysteine mini-domain selected from CxxC (SEQ ID NO 3), CxxxC (SEQ ID NO 4) or CxxxxC (SEQ ID NO 5) is present in the LH, MPH or TMD where x represents any amino acids; and wherein CFLLC is excluded if the CxxxC (SEQ ID NO 4) is to be presented in the TMD; whereby when the recombinant HA antigenic protein forms a trimer, the two cysteines in the LH, MPH or TMD form a tandem disulfide bond belt, covalently tightening the trimer.

In another embodiment of the recombinant influenza virus, the TMD or CPD are derived from a HA protein that is not the same HA protein providing the extracellular domain and LH.

In another embodiment of the recombinant influenza virus, the TMD or CPD are artificially synthetic peptides or derived from a non-HA protein forming trimers in its native configuration.

In another embodiment of the recombinant influenza virus, it is used in a vaccine against influenza virus infection. In a further embodiment, the vaccine is comprised of the recombinant influenza virus that is attenuated. In another further embodiment, the vaccine is comprised of inactivated viral particles from a virus preparation of the recombinant influenza virus.

The objectives and advantages of the invention will become apparent from the following detailed description of preferred embodiments thereof in connection with the accompanying drawings.

BRIEF DESCRIPTION OF THE DRAWINGS

Preferred embodiments according to the present invention will now be described with reference to the FIGURES, in which like reference numerals denote like elements.

FIG. 1 is a functional domain block diagram of a HA protein, where the relevant domains are labeled.

DETAILED DESCRIPTION OF THE INVENTION

The present invention may be understood more readily by reference to the following detailed description of certain embodiments of the invention.

Throughout this application, where publications are referenced, the disclosures of these publications are hereby incorporated by reference, in their entireties, into this application in order to more fully describe the state of art to which this invention pertains.

The practice of the present invention will employ, unless otherwise indicated, conventional techniques of molecular biology (including recombinant techniques), microbiology, cell biology, biochemistry, nucleic acid chemistry, and immunology, which are within the skill of the art. Such techniques are explained fully in the literature, such as, *Molecular Cloning: A Laboratory Manual*, third edition (Sambrook and Russel, 2001); *Animal Cell Culture* (R. I. Freshmey, ed., 1987); *Current Protocols in Molecular Biology* (F. M. Ausubel et al., eds., 1987, including supplements through 2001); *Current Protocols in Immunology* (J. E. Coligan et al., eds., 1991); *The Immunoassay Handbook* (D. Wild, ed., Stockton Press NY, 1994); *Methods of Immunological Analysis* (R. Masseyeff, W. H. Albert, and N. A. Staines, eds., Weinheim:VCH Verlags gesellschaft mbH, 1993).

The surface of an influenza virus contains two antigens, hemagglutinin (HA) and neuraminidase (NA), where the HA is considered as the major antigen. HA has 16 subtypes (H1-H16); their coding sequences and amino acid sequences are varied. Here, one exemplary HA (H3) is shown in SEQ ID NO 1 (coding sequence) and SEQ ID NO 2 (amino acid sequence), where the amino acid sequence shown in SEQ ID NO 2 contains a signal peptide of 17 amino acids, thus all of the following description will employ the numbering system by which the amino acid of 18 is numbered as 1.

HA is initially translated into a single molecule HA0, and then the HA0 is cleaved by a protease into HA1 (aa 1-328) and HA2 (329-549), where the HA1 and HA2 are covalently linked by a inter-chain disulfide bond. HA1 contains most of, if not all, antigenic epitopes, and HA2 contains a fusion peptide, a long helix (LH) (aa 405-458), a membrane proximity helix (MPH) (aa 492-511), a transmembrane domain (TMD) (aa 512-538) and a cytoplasmic domain (CPD) (aa 539-549). The functional domain diagram in a HA molecule is shown in FIG. 1, where only the relevant domains including HA1, LH, MPH, TMD and CPD are labeled. While their sequences vary, their structures share similar domains. HA has a trimeric structure, protruding on the virus surface as a spike. It is believed that the LH, MPH, and TMD are responsible for the formation and stabilization of HA's trimer structure. In addition, the LH is involved in the formation of a triple-stranded coiled coil which stabilizes the trimer; it may explain why HA maintains its trimer configuration after the transmembrane and cytoplasmic domains are removed. It is to be noted that HA1 and HA2 can be present as a single polypeptide without cleavage for being used as an antigen in a vaccine or other functions even though the cleavage is critical for virus infection.

Previous studies showed that monoclonal antibodies recovered from patients with natural infections or immunized mice can cross react with different subtypes of influenza viruses; for example, a monoclonal antibody from a person immunized with seasonal vaccines is able to cross react with H1, H5 and H9. Most of the cross reactive mAbs are directed to the stem region of HA, but in 2011 after the provisional application was filed, one mAb was shown to bind to the receptor-binding region of HA. All these studies suggest that the trimeric HAs do contain some antigenic epitopes that are shared by most or even all of influenza A viruses; unfortunately the cross reactive antibodies against the shared antigenic epitopes produced by immunization with current seasonal vaccines or natural infections are too low to provide any meaningful protection against antigenic variants, let alone pandemic strains. If an influenza vaccine can elicit enough cross reactive antibodies against the shared antigenic epitopes, it will provide cross protection against inter-subtypic or intra-subtypic variants (a universal vaccine). However, the challenge is how we could manipulate the influenza virus (i.e., HA antigen) to achieve this goal.

The present invention hypothesized that the paucity of cross reactive antibodies in immunized or infected subjects might be due to less shared antigenic epitopes present in the current vaccines or during infection and further that the reason for the less shared antigenic epitopes present in the current vaccines is that natural HA structures especially H1, H5 and H9 do not offer sufficient stability to preserve the shared antigenic epitopes. Thus, if the stability of the HA structures can be increased, it is reasonably to expect the increases of the presence of the shared antigenic epitopes. However, the challenge is how to stabilize HA structures.

In our daily lives, a bundle of parallel materials such as bamboos and hays is held tightly by belts. Now the questions were whether HA contains any bundle of parallel structures and further whether any belt could be introduced into the bundle of parallel structures of HA if such bundle is present.

For the first question, the present invention analyzed the HA structure as described above. HA2 contains at least three helices (i.e., LH, MPH and TMD); the peptide helix has a cylindrical configuration; thus each helix in HL, MPH or TMD forms a bundle of three parallel helices inside the HA timer; it provides the physical basis for introducing one or more belts covalently connecting all three HA monomers.

For the second question, the present invention recalled that the disulfide bond (S—S) formed by two cysteines can be formed between two peptides; for example, HA1 and HA2 are covalently connected by a disulfide bond, and IgG is a homodimer bounded by multiple inter-peptide disulfide bonds. However, one cysteine in the corresponding position of each of the three monomers in a HA trimer will allow the formation of one disulfide bond but leaving one SH group free. More critically, no circular belt around all three HA monomers is formed. In order to form a circular belt, the present invention explored whether it was feasible to introduce a pair of cysteines into each monomer so that a tandem of three disulfide bonds could be formed between the three monomers. As known, each turn in a helix contains 3.6 amino acids, where the pitch (advance per turn) is 0.54 nm, and the rise (advance per amino acid residue) is 0.15 nm. For a disulfide bond formed by two cysteines, the distance between their centers is 0.849 nm (two c-c bonds (0.154 nm per bond), two c-s bonds (0.17 nm per bond), and one s-s bond (0.201 nm)). The distance of 0.849 nm is about 1.57 pitch or 5.66 amino acids; it means that if two cysteines are not separated by more than 4 amino acids, a disulfide bond could be formed between two helices.

The present invention discovered that introduction of at least one pair of cysteines into the LH, MPH and/or TMD of HA could enhance the cross reactive immune responses; the introduction was made on the assumption that the pair of cysteines could form a disulfide bond belt around the trimeric HA structure, gripping the HA trimers more tightly. While no change of stability was actually measured for lack of means, the end results of enhanced cross reactive immune responses justified this assumption.

The present invention provides that the introduction of at least one pair of cysteines forming one of the three two-cysteine mini-domains ((CxxC (SEQ ID NO 3); CxxxC (SEQ ID NO 4); CxxxxC (SEQ ID NO 5)) into HA's helix regions (LH, MPH and TMD) enables the formation of a tandem disulfide bond belt between the three monomers, where the 'x' in the mini-domains is any amino acids as long as they do not break the helix structure, preferably A, L, M, F, E, Q, H, K and R in an artificially created mini-domain. Illustratively, the three disulfide bonds between three monomers (monomer 1 with 1C1 and 1C2; monomer 2 with 2C1 and 2C2; monomer 3 with 3C1 and 3C2) are 1C1-2C2, 2C1-3C2, and 3C1-1C2. This tandem disulfide bond belt tightly grips the three monomers together to form a highly stabilized trimer. This discovery is of great significance because any trimeric protein represented by HAs could be manipulated to include at least one two-cysteine mini-domain so that the trimeric structure is stabilized by a covalent bond belt. When such HAs are used as antigens for vaccines in the forms of recombinant proteins, VLP or viruses, the vaccines would elicit enhanced intra-subtype or inter-subtype immune responses. It is surprising to note that the search for the presence of any two-cysteine mini-domains in the NCBI' protein database uncovered only one two-cysteine mini-domain (CFLLC) falling into CxxxC (SEQ ID NO 4) that is present in the TMD of H3 HA. H1-H5 and H7-H16 do not contain any two-cysteine mini-domains. The consensus TMD amino acid sequences of H1-H16 are presented in SEQ ID NOs 6-21 respectively and summarized in Table 1, where the cysteine is highlighted.

TABLE 1

The exemplary sequences of TM and CP domains of H1-H16

| | | |
|---|---|---|
| H1 | QILAIYSTVASSLVLLVSLGAISFWMC | SEQ ID NO 6 |
| H2 | QILAIYATVAGSLSLAIMIAGISFWMC | SEQ ID NO 7 |
| H3 | DWILWISFAISCFLLCVVLLGFIMWAC | SEQ ID NO 8 |
| H4 | DIILWISFSISCFLLVALLLAFILWAC | SEQ ID NO 9 |
| H5 | QILSIYSTVASSLALAIMVAGLSLWMC | SEQ ID NO 10 |
| H6 | QILAIYSTVSSSLVLVGLIIAMGLWMC | SEQ ID NO 11 |
| H7 | DVILWFSFGASCFILLAIAMGLVFICV | SEQ ID NO 12 |
| H8 | KILSIYSTVAASLCLAILIAGGLILGM | SEQ ID NO 13 |
| H9 | KILTIYSTVASSLVLAVGFAAFMFWAM | SEQ ID NO 14 |
| H10 | DIILWFSFGASCFILLAVVMGLVFFCL | SEQ ID NO 15 |
| H11 | KILSIYSCIASSLVLAAIIMGFIFWAC | SEQ ID NO 16 |
| H12 | KILSIYSSVASSLVLLLMIIGGFIFGC | SEQ ID NO 17 |
| H13 | KALSIYSCIASSVVLVGLILSFIMWAC | SEQ ID NO 18 |
| H14 | DIILWISFSMSCFVFVALILGFVLWAC | SEQ ID NO 19 |
| H15 | DVILWFSFGASCVMLLAIAMGLIFMCV | SEQ ID NO 20 |
| H16 | KVLSIYSCIASSIVLVGLILAFIMWAC | SEQ ID NO 21 |

The two-cysteine mini-domain (CFLLC) falling into CxxxC (SEQ ID NO 4) present in the TMD of H3HA lends the support to the practicality of the present invention. We further searched the literature and found no specific study of the functions of the unique mini-domain. Interestingly, some studies among a vast of literature studying inter-subtpyic cross immune responses reported that mucosal immunization of inactivated virus vaccine of H3N2 did show partial inter-subtypic cross protection against H1N1 or H5N1, but all these reports concluded that the elicited inter-subtypic cross protection was due to the unique immunization route (i.e., mucosal immunization), teaching the researchers away from exploring of whether H3N2 virus has any special structure features that could be responsible for the achieved cross protection, let alone the CFFLC mini-domain.

The introduction of a tandem disulfide bond belt into a recombinant HA protein can be achieved using any suitable molecular biological methods, for example point mutation, insertion or replacement; they are well established and known in the art. The exemplary embodiments of producing the recombinant HA protein include: (1) mutating two amino acid resides into cysteines in any of HA helixes (LH, MPH or TMD) to form a two-cysteine mini-domain with a sequence selected from CxxC (SEQ ID NO 3), CxxxC (SEQ ID NO 4), or CxxxxC (SEQ ID NO 5); as shown in Table 1, the H3 TMD (SEQ ID NO 8) contains one two-cysteine mini-domain CFLLC (falling into SEQ ID NO 4) in the positions of 12 and 16 (the amino acids of TMD are numbered from 1-27); this will be an exception for the present invention; in addition, if one cysteine is present already (e.g., H4 TMD (SEQ ID NO 9)), the mutation of one amino acid is needed; (2) inserting a two-cysteine mini-domain into any of HA helixes (LH, MPH or TMD) as long as the insertion does not break the helix structure; (3) replacing a corresponding stretch of amino acids in any of HA helixes (LH, MPH or TMD) with one synthetic polypeptide containing a two-cysteine mini-domain; (4) replacing a corresponding stretch of amino acids in any of HA helixes (LH, MPH or TMD) with the one from one natural molecule containing a two-cysteine mini-domain for example CFFLC from H3TMD; (5) fusing the extracellular domain of HA to the transmembrane domain and cytoplasmic tail of another protein, where the fused transmembrane contains at least one two-cysteine mini-domain, for example, the extracellular domains of H1-H2 and H4-H16 can be fused to the transmembrane/cytoplasmic domains of H3.

In some embodiments, the HA's LH and MPH can be manipulated so as to contain at least one two-cysteine mini-domain that enables to form a tandem disulfide bond belt in the trimers. This would allow express a soluble form of trimers that are covalently stabilized.

In some embodiment, two or more two-cysteine mini-domains can be introduced into one HA recombinant protein.

One embodiment of the present invention provides a recombinant HA antigenic protein comprising an extracellular domain with major antigenic epitopes, a long helix (LH), a membrane-proximity helix (MPH), a transmembrane domain (TMD) and a cytoplasmic domain(CPD), wherein at least one two-cysteine mini-domain selected from CxxC (SEQ ID NO 3), CxxxC (SEQ ID NO 4) or CxxxxC (SEQ ID NO 5) is present in the LH, MPH or TMD. In some embodiments, the authetic TMD or CPD from HA proteins is modified to contain one or more two-cysteine mini-domains. In some embodiments, the TMD or CPD are derived from other trimeric molecules for example HIV Env molecules. In some embodiments, the TMD or CPD can be artificially synthetic. The recombinant HA antigenic protein can be expressed in any suitable system as long as the expression system produces effective recombinant HA antigenic protein for vaccine use, for example yeast, insect cell or mammalian cell expression systems are suitable.

Another embodiment of the present invention provides a soluble recombinant HA antigenic protein comprising an extracellular domain of HA protein with major antigenic epitopes, and a LH without the transmembrane domain (TMD) and cytoplasmic domain(CPD), wherein at least one two-cysteine mini-domain selected from CxxC (SEQ ID NO 3), CxxxC (SEQ ID NO 4) or CxxxxC (SEQ ID NO 5) is present in the LH. The soluble recombinant HA antigenic protein can be expressed in any suitable system as long as the expression system produces effective recombinant HA antigenic protein for vaccine use, for example yeast, insect cell or mammalian cell expression systems are suitable.

Another embodiment of the present invention provides an in vivo expression vector comprising an encoding sequence encoding a recombinant HA antigenic protein, where the recombinant HA antigenic protein comprises an extracellular domain with major antigenic epitopes, a long helix (LH), a membrane-proximity helix (MPH), a transmembrane domain (TMD) and a cytoplasmic domain(CPD), wherein at least one two-cysteine mini-domain selected from CxxC (SEQ ID NO 3), CxxxC (SEQ ID NO 4) or CxxxxC (SEQ ID NO 5) is present in the LH, MPH or TMD. In some embodiments, the authetic TMD or CPD from HA proteins is modified to contain one or more two-cysteine mini-domains. In some embodiments, the TMD or CPD are derived from other trimeric molecules for example HIV Env molecules. In some embodiments, the TMD or CPD can be artificially synthetic. The expression vector is used as DNA vaccines; the exemplary expression vectors include lentivirus expression vector, adenovirus expression vector, adeno-associated virus expression vector or other mammalian expression vectors. For example, the encoding sequence for the HA recombinant protein is cloned into a CMV/R expression vector for efficient expression in mammalian cells.

Another embodiment of the present invention provides a virus-like particle comprising a recombinant HA antigenic protein comprising an extracellular domain with major antigenic epitopes, a long helix (LH), a membrane-proximity helix (MPH), a transmembrane domain (TMD) and a cytoplasmic domain(CPD), wherein at least one two-cysteine domain selected from CxxC (SEQ ID NO 3), CxxxC (SEQ ID NO 4) or CxxxxC (SEQ ID NO 5) is present in the LH, MPH or TMD. In some embodiments, the authetic TMD or CPD from HA proteins is modified to contain one or more two-cysteine mini-domains. In some embodiments, the TMD or CPD are derived from other trimeric molecules for example HIV Env molecules. In some embodiments, the TMD or CPD can be artificially synthetic. The influenza VLP can be generated by any suitable methods. In some embodiments, the influenza VLP is generated by co-expressing the recombinant HA antigenic protein, influenza virus NA and M proteins. The VLP can be generated by any suitable methods that is well established and known in the art.

Another embodiment of the present invention provides a recombinant influenza virus comprising the recombinant HA antigenic protein as described above. The recombinant influenza virus can be produced by any known methods for example reverse genetics. During the production of a vaccine using the recombinant influenza virus, the virus preparation can be made following the teachings of one accompanying application entitled "Viral vaccine and process for preparing the same", in which the proportion of the subpopulation of infectious viral particles in the virus preparation is optimized.

The primary goal of the present invention is to provide an influenza virus vaccine that can elicit inter-subtypic and/or intra-subtypic cross reactive immune responses. Thus, the recombinant HA, in vivo expression vector encoding the recombinant HA, the virus-like particles and the recombinant influenza virus can all be used in a vaccine. At the same time, they can also be used in many other ways for example as an antigen to produce the cross-reactive monoclonal antibodies or to identify the binding epitopes for monoclonal antibodies.

It is to be noted that many biotech applications are lengthy for stuffing extensive materials including methods and procedures that are well established and known in the art because the biotechnology was viewed with low predictability so that the examiners might raise the rejections failing to provide adequate details for one skilled in the art to practice the invention (lack of enablement). As a biotech researcher, the inventor of the present invention firmly believes that the biotechnology as a whole has advanced enough in the past thirty years that many basic procedures are well established and known, and more importantly the results are as predictable as that in the arts of mechanic and electronic engineering. For example, with a known virus and sequences, the DNA fragments of the virus shall be certainly obtained by PCR amplification; with a DNA fragment with known sequence, it shall be predictably subcloned into any vector including expression vectors in vitro and in vivo; with a cloned expression vector, the cloned gene shall be predictably expressed and purified; a virus-like particle can also be generated with known techniques; and a recombinant influenza virus can be rescued from plasmid systems such as reverse genetics. As a patent attorney, I strongly believe that biotech patent applications have come to the age when no more unnecessary materials are stuffed into an application, just as an electronic patent application never includes the description of the function of a capacitor or an amplifier. The elimination of the stuffed unnecessary materials helps to avoid the waste of time for both examiners and clients, and also makes the principles of the invention to be easily understood. In view of this, the known methods and materials are not included in this application.

As used herein, a "vaccine" is an antigenic preparation that is used to induce an immune response in individuals. A vaccine can have more than one constituent that is antigenic.

As used herein, "non-protein carriers" are carriers which are not proteins and can be used to achieve multimeric display of influenza matrix and/or nucleoprotein.

The term "microcarrier" refers to a particulate composition which is insoluble in water and which has a size of less than about 150, 120 or 100 um, more commonly less than about 50-60 um, and may be less than about 10 um or even less than about 5 um. Microcarriers include "nanocarriers," which are microcarriers have a size of less than about 1 um, preferably less than about 500 nm. Microcarriers include solid phase particles such particles formed from biocompatible naturally occurring polymers, synthetic polymers or synthetic copolymers, although microcarriers formed from agarose or cross-linked agarose may be included or excluded from the definition of microcarriers herein as well as other biodigradable materials known in the art. Solid phase microcarriers are formed from polymers or other materials which are non-erodible and/or non-degradable under mammlian physiological conditions, such as polystyrene, polypropylene, silica, ceramic, polyacrylamide, gold, latex, hydroxyapatite, and ferromagnetic and paramagnetic materials. Biodegradable solid phase microcarriers may be formed from polymers which are degradable (e.g., poly(lactic acid), poly(glycolic acid) and copolymers thereof, such as poly(D, L-lactide-co-glycolide) or erodible (e.g., poly(ortho esters such as 3,9-diethylidene-2,4,8,10-tetraoxaspiro[5,5]undecane (DETOSU) or poly(anhydrides), such as poly(anhydrides) of sebacic acid) under mammalian physiologicaly conditions. Microcarriers are typically spherical in shape, but microcarriers which deviate from spherical shape are also acceptable (e.g., ellipsoidal, rod-shaped, etc.). Due to their insoluble nature, some solid phase microcarriers are filterable from water and water-based (aqueous) solutions (e.g., using a 0.2 micron filter). Microcarriers may also be liquid phase (e.g., oil or lipid based), such as liposomes, iscoms (immune-stimulating complexes, which are stable complexes of cholesterol, phospholipid and adjuvant-active saponin) without antigen, or droplets or micelles found in oil-in-water or water-in-oil emulsions, such as MF59. Biodegradable liquid phase microcarriers typically incorporate a biodegradable oil, a number of which are known in the art, including squalene and vegetable oils. The term "nonbiodegradable", as used herein, refers to a microcarrier which is not degraded or eroded under normal mammalian physiological conditions. Generally, a microcarrier is considered nonbiodegradable if it no degraded (i.e., loses less than 5% of its mass or average polymer length) after a 72 hour incubation at 37 oC in normal human serum.

An "individual" or "subject" is a vertebrate including avian (such as chickens, ducks and geese), and a mammal. Mammals include, but are not limited to, humans, non-human primates, farm animals, sport animals, experimental animals, rodents (e.g., mice and rats) and pets.

An "effective amount" or a "sufficient amount" of a substance is that amount sufficient to effect a desired biological effect, such as beneficial results, including clinical results, and as such, an "effective amount" depends upon the context in which it is being applied. In the context of this invention, an example of an effective amount of a composition comprising the desired antigen is an amount sufficient to induce an immune response in an individual. An effective amount can be administered in one or more administrations.

"Stimulation" of an immune response, such as humoral or cellular immune response, means an increase in the response, which can arise from eliciting and/or enhancement of a response.

As used herein, and as well-understood in the art, "treatment" is an approach for obtaining beneficial or desired results, including clinical results. For purposes of this invention, beneficial or desired clinical results include, but are not limited to, alleviation or amelioration of one or more symptoms, diminishment of extent of infection, stabilized (i.e., not worsening) state of infection, amelioration or palliation of the infectious state, and remission (whether partial or total), whether detectable or undetectable. "Treatment" can also mean prolonging survival as compared to expected survival if not receiving treatment.

According to the present invention, a "dose" of a vaccine composition, is a quantity of vaccine composition that is administered at a particular point in time. A "dose" may also be a quantity of vaccine composition that is gradually administered to an animal using an extended release formulation and/or apparatus. In certain embodiments of the present invention, two or more doses of the vaccine composition are administered to an animal at different time points.

According to the present invention, an "immunologically-effective amount" of an influenza virus (e.g., an inactivated influenza virus) is an amount of influenza virus (usually expressed in terms of hemagglutinating units or "HA units") which will induce complete or partial immunity in a treated animal against subsequent challenge with a virulent strain of avian influenza virus. Complete or partial immunity can be assessed by observing, either qualitatively or quantitatively, the clinical symptoms of influenza virus infection in a vaccinated animal as compared to an unvaccinated animal after being challenged with virulent strains of avian influenza virus. Where the clinical symptoms of influenza virus infection in a vaccinated animal after challenge are reduced, lessened or eliminated as compared to the symptoms observed in an unvaccinated animal after a similar or identical challenge, the amount of influenza virus that was administered to the vaccinated animal is regarded as an "immunologically-effective amount".

A "cross-protective immune response" is one which protects against infection by a virus strain which is not identical to the one used to elicit the response.

As will be understood in the art, an "adjuvant" means one or more substances that enhance the immunogenicity and/or efficacy of a vaccine composition. Non-limiting examples of suitable adjuvants include squalane and squalene (or other oils of animal origin); block copolymers; detergents such as Tween-80; Quil A, mineral oils such as Drakeol or Marcol, vegetable oils such peanut oil; *Corynebacterium*-derived adjuvants such as *Corynebacterium parvum; Propionibacterium*-derived adjuvants such as *Propionibacterium acne; Mycobacterium bovis* (Bacille Calmette and Guerin or BCG); interleukins such as interleukin 2 and interleukin 12; monokines such as interleukin 1; tumor necrosis factor; interferons such as gamma interferon; surface active substances such as hexadecylamine, octadecylamine, octadecyl amino acid esters, lysolecithin, dimethyldioctadecylammonium bromide, N,N-dicoctadecyl-N',N'bis)2-hydroxyethyl-propanediamine), methoxyhexadecylglycerol, and pluronic polyols; polyamines such as pyran, dextransulfate, poly IC carbopol; peptides such as muramyl dipeptide and derivatives, dimethylglycine, tuftsin; oil emulsions; and mineral gels such as aluminum phosphate, aluminum hydroxide or alum; combinations such as saponin-aluminium hydroxide or Quil-A aluminium hydroxide; liposomes; mycobacterial cell wall extract; synthetic glycopeptides such as muramyl dipeptides or other derivatives; Avridine; Lipid A derivatives; dextran sulfate; DEAE-Dextran or with aluminium phosphate; carboxypolymethylene such as Carbopol'EMA; acrylic copolymer emulsions such as Neocryl A640; vaccinia or animal poxvirus proteins; sub-viral particle adjuvants such as cholera toxin, or mixtures thereof.

A therapeutic composition of the present invention can be formulated in an excipient that the object to be treated can tolerate. Examples of such excipients include water, saline, Ringer's solution, dextrose solution, Hank's solution, and other aqueous physiologically balanced salt solutions. Excipients can also contain minor amounts of additives, such as substances that enhance isotonicity and chemical or biological stability. Examples of buffers include phosphate buffer, bicarbonate buffer, and Tris buffer, while examples of stabilizers include A1/A2 stabilizer, available from Diamond Animal Health, Des Moines, Iowa.

Acceptable protocol to administer therapeutic compositions in an effective manner includes individual dose size, number of doses, frequency of dose administration, and mode of administration. Determination of such protocols can be accomplished by those skilled in the art, and examples are disclosed herein.

Administering or administer is defined as the introduction of a substance into the body of an individual and includes oral, nasal, ocular, rectal, vaginal and parenteral routes. Compositions may be administered individually or in combination with other agents via any route of administration, including but not limited to subcutaneous (SQ), intramuscular (IM), intravenous (IV), intraperitoneal (IP), intradermal (ID), via the nasal, ocular or oral mucosa (IN) or orally.

The dose administered to a patient, in the context of the present invention, should be sufficient to effect a beneficial response in a patient over an appropriate period of time. The quantity of agents to be administered may depend on the subject to be treated inclusive of the age, sex, weight and general health condition thereof, factors that will depend on the judgment of the practitioner.

Immunotherapeutic compositions of the invention may be used to prophylactically or therapeutically immunize animals such as humans. However, other animals are contemplated, preferably vertebrate animals including domestic animals such as livestock and companion animals.

The vaccine may be used in combination with others; for example, priming with an attenuated vaccine follows with a boost using the inactivated vaccine.

The invention encompasses all pharmaceutical compositions comprising an antigen, an adjuvant, and a pharmeceutically acceptable carrier.

Pharmaceutically acceptable carriers preferred for use in the present invention may include sterile aqueous of non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose", and the like. Preservatives and other additives may also be present such as, for example, antimicrobials, antioxidants, chelating agents, and inert gases and the like.

EXAMPLES

The following examples are provided for the sole purpose of illustrating the principles of the present invention; they are by no means intended as limitations of the present invention.

I. Recombinant HA Antigenic Protein

HA was from PR8, a well known H1N1 virus. The amino acid sequence of wild type H1HA is shown in SEQ ID NO 22 (565 amino acids); the recombinant H1HA is shown in SEQ ID NO 23, where two amino acids in the TMD were mutated into cysteines (S538C and L542C), designated as H12C. The mutations were achieved by the point mutation method.

Both H1WT and H12C were subcloned into a pFast-Bac vector (Invitrogen, Carlsbad, Calif., USA) first, and the baculovirus recombinants (rBacH1WT and rBacH12C) were prepared and used to infect *Spodoptera frugiperda* Sf9 cells to express the recombinant HA proteins. The expressed recombinant H1WT and H12C were purified and verified by Western blot; their functions were tested.

II. In vivo Expression Vector Comprising the Recombinant HA Antigenic Protein

H1WT and H12C are cloned into in vivo expression vectors such as adenovirus vectors, vaccinia vectors, adeno-associated virus vectors, lentivirus vectors. They are used for DNA vaccine for immunization. Their efficiency for eliciting cross reactive immune responses is tested for their cross-reaction with inter-subtypic (e.g., H3N2, H5N1) or intra-subtypic viruses.

III. Virus-Like Particles Comprising the Recombinant HA Antigenic Protein

1. Cell Lines

*Spodoptera frugiperda* Sf9 cells were maintained in serum-free SF900II medium (GIBCO, Grand Island, N.Y.) at 28° C. in spinner flasks at a speed of 100 rpm.

2. Generation of Recombinant Baculoviruses

A Bac-to-Bac baculovirus expression system is used for the generation of recombinant baculoviruses vectors expressing a recombinant HA protein (H1WT (SEQ ID NO 22), H12C (SEQ ID NO 23)). Other components are also amplified from PR8. Followed by PCR using specific primers annealing to the 3' and 5' terminus of each gene, fragments containing HA, NA, M1 and NP genes are cloned into the pFast-Bac-Dual vector (Invitrogen, Carlsbad, Calif., USA). Recombinant bacmids are generated by site-specific homologous recombination and transformation of the influenza genes-containing plasmid into *E. coli* DH10-Bac competent cells, which contained the AcMNPV baculovirus genome (Invitrogen). 1 μg of purified recombinant bacmid DNA is transfected into Spodoptera frugiperda Sf9 insect cells seeded in 6-well plates at 5×10⁵ cells/ml using CellFectin reagent (Invitrogen). Cells are incubated for 3 days, and the virus harvested from the supernatant is subjected to three rounds of plaque purification.

3. Formation and Purification of Influenza VLPs

Influenza VLPs are attained by co-infection of Sf9 insect cells with baculovirus recombinants. Sf9 cells are seeded at a density of 2×10⁶ per flask and allowed to settle at room temperature for 30 min. Subsequently, the Sf9 insect cells are co-infected with rBVs at multiplicities of infection (MOI) of 3-5 and incubated for 72 h at 28° C. Culture supernatant (200 ml) from Sf9 cells are harvested and clarified by centrifugation for 30 min at 2000×g at 4° C. The VLPs in the supernatant are pelleted by ultracentrifugation for 60 min at 100,000×g at 4° C. The sedimented particles resuspended in 1 ml of phosphate buffered saline (PBS) solution (pH 7.2) are loaded onto a 20%-30%-60% (w/v) discontinuous sucrose step density gradient and sedimented by ultracentrifugation for 60 min at 100,000×g at 4° C. The VLPs bands are collected and analyzed by SDS-PAGE and Western blot.

IV. Recombinant Influenza Virus Comprising the Recombinant HA Antigenic Protein

Reverse genetics was employed to produce the recombinant influenza virus. Two recombinant influenza viruses were rescued, one containing H1WT and one containing H12C; both shared the same genetic background (i.e., the remaining seven segments were derived from PR8). The rescued recombinant influenza viruses were amplified in embryonated chicken eggs, and inactivated with 0.1% formalin. The inactivated viruses were mixed with complete Freud adjuvant to produce the vaccine (5 ug/dose) for the first immunization of Balb/c mice (5 per group); for the second immunization, incomplete Freud adjuvant was used. Two weeks after the second immunization, the sera were obtained from different groups and tested against one H3N2 strain virus using ELISA. The ELISA results (sera were diluted 1,600 times) are shown in the Table 2.

TABLE 2

ELISA results of H1WT sera and H12C sera against purified H1WT, H12C and H3N2

| Serum source | H1WT | H12C | H3N2 |
|---|---|---|---|
| H1WT | 0.784 | 0.708 | 0.166 |
| H12C | 0.426 | 0.563 | 0.219 |

From Table 2, the sera from the group immunized with H12C had a lower titer than that from the group immunized with H1WT when they are compared with titers against H1WT and H12C antigens. However, the titer against H3N2 from H12C is higher than that from H1WT, demonstrating that the introduction of a pair of two cysteines forming a CxxxC mini-domain (SEQ ID NO 4) into the TMD of H1 HA increased its capacity of eliciting stronger cross-reactive immune responses.

While the present invention has been described with reference to particular embodiments, it will be understood that the embodiments are illustrative and that the invention scope is not so limited. Alternative embodiments of the present invention will become apparent to those having ordinary skill in the art to which the present invention pertains. Such alternate embodiments are considered to be encompassed within the spirit and scope of the present invention. Accordingly, the scope of the present invention is described by the appended claims and is supported by the foregoing description.

What is claimed is:

1. A recombinant HA antigenic protein, comprising:
an extracellular domain; and
a long helix (LH);
wherein at least one two-cysteine mini-domain selected from CxxC (SEQ ID NO 3), CxxxC (SEQ ID NO 4) or CxxxxC (SEQ ID NO 5) is present in the LH, where x represents any amino acid as long as it does not break the helix structure.

2. The recombinant HA antigenic protein, comprising:
an extracellular domain;
a long helix (LH);
a membrane-proximity helix (MPH);
a transmembrane domain (TMD); and
a cytoplasmic domain(CPD);
wherein the at least one two-cysteine mini-domain selected from CxxC (SEQ ID NO 3), CxxxC (SEQ ID NO 4) or CxxxxC (SEQ ID NO 5) is present in the LH, MPH or TMD, where x represents any amino acid as long as it does not break the helix structure, and wherein CFLLC is excluded if the CxxxC (SEQ ID NO 4) is to be presented in the TMD (SEQ ID NO 8) of a H3 HA.

3. The recombinant HA antigenic protein of claim 2, wherein the TMD or CPD are derived from a HA protein that is not the same HA protein providing the extracellular domain and LH.

4. The recombinant HA antigenic protein of claim 2, wherein the TMD or CPD is artificially synthetic peptides or derived from a non-HA protein that forms trimers in its native configuration.

5. The recombinant HA antigenic protein of claim 1, wherein the recombinant HA antigenic protein is encoded by a DNA sequence, and the DNA sequence is cloned into an in vivo expression vector; so that the recombinant HA expression vector is used as a DNA vaccine against influenza virus infection.

6. The recombinant HA antigenic protein of claim 2, wherein the recombinant HA antigenic protein is encoded by a DNA sequence, and the DNA sequence is cloned into an in vivo expression vector; so that the recombinant HA expression vector is used as a DNA vaccine against influenza virus infection.

7. The recombinant HA antigenic protein of claim 1, wherein the recombinant HA antigenic protein is used in a vaccine against influenza virus infection.

8. The recombinant HA antigenic protein of claim 2, wherein the recombinant HA antigenic protein is used in a vaccine against influenza virus infection.

9. The recombinant HA antigenic protein of claim 1, wherein the recombinant HA antigenic protein is incorporated into a virus-like particle.

10. The recombinant HA antigenic protein of claim 2, wherein the recombinant HA antigenic protein is incorporated into a virus-like particle.

11. The recombinant HA antigenic protein of claim 1, wherein the recombinant HA antigenic protein is incorporated into a recombinant influenza virus.

12. The recombinant HA antigenic protein of claim 2, wherein the recombinant HA antigenic protein is incorporated into a recombinant influenza virus.

* * * * *